(12) United States Patent  (10) Patent No.: US 8,053,625 B2
Nhan et al.  (45) Date of Patent: Nov. 8, 2011

(54) ABSORBENT ARTICLES INCLUDING A BODY FLUID SIGNALING DEVICE

(75) Inventors: Davis Dang H. Nhan, Appleton, WI (US); Andrew M. Long, Appleton, WI (US); Shirlee A. Weber, Neenah, WI (US); Darold D. Tippey, Neenah, WI (US); Meghan E. Collins, Palatine, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1363 days.

(21) Appl. No.: 11/639,973

(22) Filed: Dec. 14, 2006

(65) Prior Publication Data

US 2008/0147030 A1 Jun. 19, 2008

(51) Int. Cl.
*A61F 13/15* (2006.01)
(52) U.S. Cl. .................. 604/361; 600/362; 436/169
(58) Field of Classification Search .................. 604/361; 436/169–171; 600/362; 73/61.52, 6.54
See application file for complete search history.

(56) References Cited

U.S. PATENT DOCUMENTS

| | | |
|---|---|---|
| 2,905,169 A | 9/1959 | Nieburgs |
| 3,731,685 A | 5/1973 | Eidus |
| 3,794,024 A | 2/1974 | Kokx et al. |
| 3,918,454 A | 11/1975 | Korodi et al. |
| 3,952,746 A | 4/1976 | Summers |
| 4,022,211 A | 5/1977 | Timmons et al. |
| 4,057,029 A * | 11/1977 | Seiter .................. 374/106 |
| 4,100,324 A | 7/1978 | Anderson et al. |
| 4,231,370 A * | 11/1980 | Mroz et al. .................. 604/361 |
| 4,266,022 A | 5/1981 | Lamprecht |
| 4,287,153 A | 9/1981 | Towsend |
| 4,327,731 A | 5/1982 | Powell |
| 4,507,121 A | 3/1985 | Leung |
| 4,666,833 A | 5/1987 | Roy et al. |
| 4,704,116 A | 11/1987 | Enloe |
| 4,724,204 A | 2/1988 | Steinbach et al. |
| 4,738,674 A | 4/1988 | Todd et al. |
| 4,843,014 A | 6/1989 | Cukier |
| 4,910,803 A | 3/1990 | Cukier |
| 4,931,051 A | 6/1990 | Castello |
| 4,940,464 A | 7/1990 | Van Gompel et al. |
| 4,955,876 A | 9/1990 | Millner |
| D313,076 S | 12/1990 | Harju |
| 5,091,153 A | 2/1992 | Bachand |
| 5,173,433 A | 12/1992 | Bachand |
| 5,181,905 A | 1/1993 | Flam |
| D337,064 S | 7/1993 | Basile |
| 5,284,703 A | 2/1994 | Everhart et al. |
| 5,350,624 A | 9/1994 | Georger et al. |
| 5,354,289 A | 10/1994 | Mitchell et al. |
| 5,486,166 A | 1/1996 | Bishop et al. |

(Continued)

FOREIGN PATENT DOCUMENTS

DE 44 03 437 A1 8/1995

(Continued)

*Primary Examiner* — Lynne Anderson
(74) *Attorney, Agent, or Firm* — Randall W. Fieldhack (57) ABSTRACT

Wetness indicators may include alarm devices that are designed to assist parents or attendants in identifying a wet diaper condition early on. These devices produce either a visual or an audible signal. Many of these devices rely on electronics, which may increase the expense of the absorbent article. Further, electronic devices rely on electrical sources and may be prone to failure if not utilized for an extended period of time.

14 Claims, 6 Drawing Sheets

U.S. PATENT DOCUMENTS

| | | | |
|---|---|---|---|
| 5,490,846 A | 2/1996 | Ellis et al. | |
| 5,690,624 A | 11/1997 | Sasaki et al. | |
| 5,733,273 A | 3/1998 | Ahr | |
| 5,766,389 A | 6/1998 | Brandon et al. | |
| 5,820,973 A | 10/1998 | Dodge, II et al. | |
| 5,902,296 A | 5/1999 | Fluyeras | |
| 6,042,264 A * | 3/2000 | Prusik et al. | 374/106 |
| 6,203,496 B1 | 3/2001 | Gael et al. | |
| 6,213,992 B1 | 4/2001 | Dreier | |
| 6,284,942 B1 | 9/2001 | Rabin | |
| 6,464,635 B1 | 10/2002 | Jimenez Cerrato et al. | |
| 6,479,727 B1 | 11/2002 | Roe | |
| 6,515,194 B2 | 2/2003 | Neading et al. | |
| 6,617,488 B1 | 9/2003 | Springer et al. | |
| 6,645,190 B1 | 11/2003 | Olson et al. | |
| 6,649,804 B2 | 11/2003 | Eakin | |
| 6,679,831 B1 | 1/2004 | Zunker et al. | |
| 6,719,691 B2 | 4/2004 | Kritzman et al. | |
| 7,365,238 B2 * | 4/2008 | Diehl et al. | 604/361 |
| 2003/0014025 A1 * | 1/2003 | Allen et al. | 604/361 |
| 2003/0130631 A1 * | 7/2003 | Springer et al. | 604/361 |
| 2004/0133090 A1 * | 7/2004 | Dostoinov et al. | 600/362 |
| 2005/0065489 A1 | 3/2005 | Driskell et al. | |
| 2005/0131287 A1 * | 6/2005 | Kaylor et al. | 600/362 |
| 2006/0025732 A1 | 2/2006 | Ying et al. | |
| 2006/0069362 A1 | 3/2006 | Odorzynski et al. | |
| 2006/0114754 A1 | 6/2006 | MacDonald et al. | |
| 2006/0229577 A1 | 10/2006 | Roe et al. | |
| 2007/0156106 A1 * | 7/2007 | Klofta et al. | 604/361 |
| 2008/0103414 A1 * | 5/2008 | Song | 600/573 |

FOREIGN PATENT DOCUMENTS

| | | |
|---|---|---|
| DE | 198 33 485 A1 | 2/2000 |
| EP | 0 021 492 B1 | 1/1984 |
| EP | 0 418 482 B1 | 11/1994 |
| EP | 0 485 940 B1 | 8/1996 |
| FR | 2695824 A1 | 10/2006 |
| GB | 1 026 451 A | 4/1966 |
| GB | 2 183 160 A | 6/1987 |
| GB | 2 327 354 A | 1/1999 |
| GB | 2 348 137 A | 9/2000 |
| JP | 2000-093455 A | 4/2000 |
| JP | 2005-000602 A | 1/2005 |
| WO | WO 94/24557 A1 | 10/1994 |
| WO | WO 00/37009 A2 | 6/2000 |
| WO | WO 02/49563 A1 | 6/2002 |
| WO | WO 03/005946 A1 | 1/2003 |
| WO | WO 2005/031351 A1 | 4/2005 |
| WO | WO 2005/061013 A1 | 7/2005 |
| WO | WO 2006/047815 A1 | 5/2006 |

* cited by examiner

ABSORBENT ARTICLES INCLUDING A BODY FLUID SIGNALING DEVICE

BACKGROUND OF THE INVENTION

Absorbent articles such as diapers, training pants, incontinence products, feminine hygiene products, swim undergarments, and the like, conventionally include a liquid permeable body-side liner, a liquid impermeable outer cover, and an absorbent core. The absorbent core is typically located between the outer cover and the liner for taking in and retaining liquids (e.g., urine) exuded by the wearer. The absorbent core can be made of, for instance, superabsorbent particles. Many absorbent articles, especially those sold under the trade name HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants in identifying a wet diaper condition early on. These devices produce either a visual or an audible signal. Many of these devices rely on electronics, which may increase the expense of the absorbent article. Further, electronic devices rely on electrical sources and may be prone to failure if not utilized for an extended period of time.

Problems, however, have been encountered in designing a signaling device that does not appreciably increase the cost of the absorbent article, while providing a meaningful signal to the caregiver without relying on an electrical source for operation.

SUMMARY OF THE INVENTION

The present inventors undertook intensive research and development efforts concerning improving absorbent articles. The present invention is directed in part to an absorbent article for absorbing a liquid including a chassis. The chassis including an outer cover having an interior surface and an exterior surface and an absorbent structure positioned adjacent the interior surface of the outer cover. The chassis including a crotch region positioned in between a front region and a back region. The front region and the back region defining a waist region therebetween. The absorbent article includes a wicking layer positioned adjacent the outer cover, where at least a receptive portion of the wicking layer is in liquid communication with the absorbent structure. The absorbent article includes a liquid barrier positioned between the absorbent structure and a diagnostic portion of the wicking layer. The diagnostic portion of the wicking layer being in liquid communication with the receptive portion of the wicking layer. The absorbent articles also include an indicator material located on the wicking layer. The indicator material includes a plurality of active constituents where the active constituents move along the wicking layer at different speeds as the liquid moves through the wicking layer.

Another aspect of the present invention is directed to an absorbent article for absorbing a liquid including a chassis. The chassis including an outer cover having an interior surface and an exterior surface and an absorbent structure positioned adjacent the interior surface of the outer cover. The chassis including a crotch region positioned in between a front region and a back region. The front region and the back region defining a waist region therebetween. The absorbent article includes a wicking layer positioned adjacent the outer cover, where at least a receptive portion of the wicking layer is in liquid communication with the absorbent structure. The wicking layer has a vertical wicking speed of less than 0.5 cm/min. The absorbent article includes a liquid barrier positioned between the absorbent structure and a diagnostic portion of the wicking layer. The diagnostic portion of the wicking layer being in liquid communication with the receptive portion of the wicking layer. The absorbent articles also include an indicator material located on the wicking layer. The indicator material includes a plurality of active constituents where the active constituents move along the wicking layer at different speeds as the liquid moves through the wicking layer. Further, the plurality of active constituents comprises visible constituents.

Another aspect of the present invention is directed to an absorbent article for absorbing a liquid including a chassis. The chassis including an outer cover having an interior surface and an exterior surface and an absorbent structure positioned adjacent the interior surface of the outer cover. The chassis including a crotch region positioned in between a front region and a back region. The front region and the back region defining a waist region therebetween. The absorbent article includes a wicking layer positioned adjacent the outer cover, where at least a receptive portion of the wicking layer is in liquid communication with the absorbent structure. The wicking layer has a vertical wicking speed of less than 0.5 cm/min. The absorbent article includes a liquid barrier positioned between the absorbent structure and a diagnostic portion of the wicking layer. The diagnostic portion of the wicking layer being in liquid communication with the receptive portion of the wicking layer. The absorbent articles also include an indicator material located on the wicking layer. The indicator material includes a plurality of active constituents where the active constituents move along the wicking layer at different speeds as the liquid moves through the wicking layer. The absorbent article also includes a timing indicia positioned from about 5 minutes to about 30 minutes from the indicator material based on the vertical wicking speed.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to absorbent articles adapted to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. Generally, the absorbent articles are disposable, meaning that they are designed to be discarded after a limited use rather than being laundered or otherwise restored for reuse.

Figure 1:
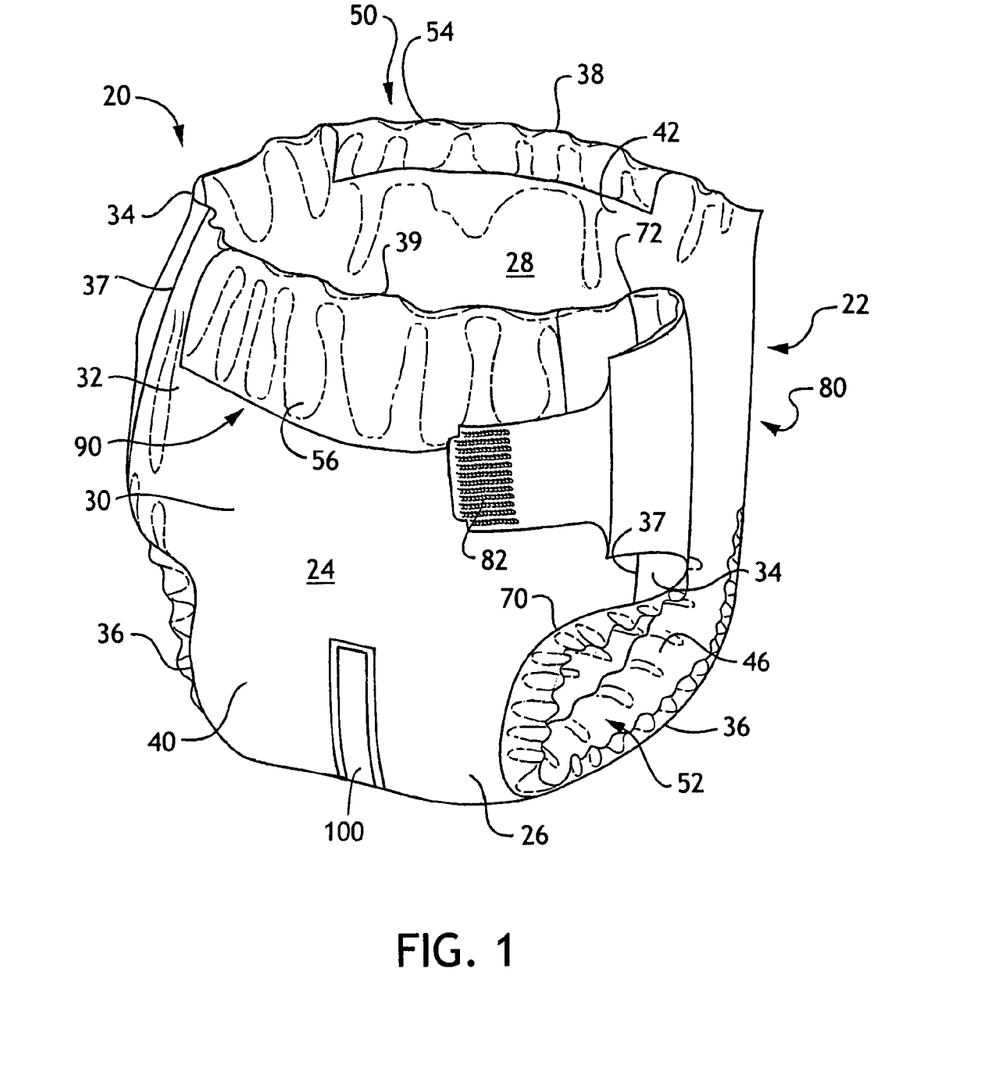
FIG. 1 is a rear perspective view of one embodiment of an absorbent article.
Figure 2:
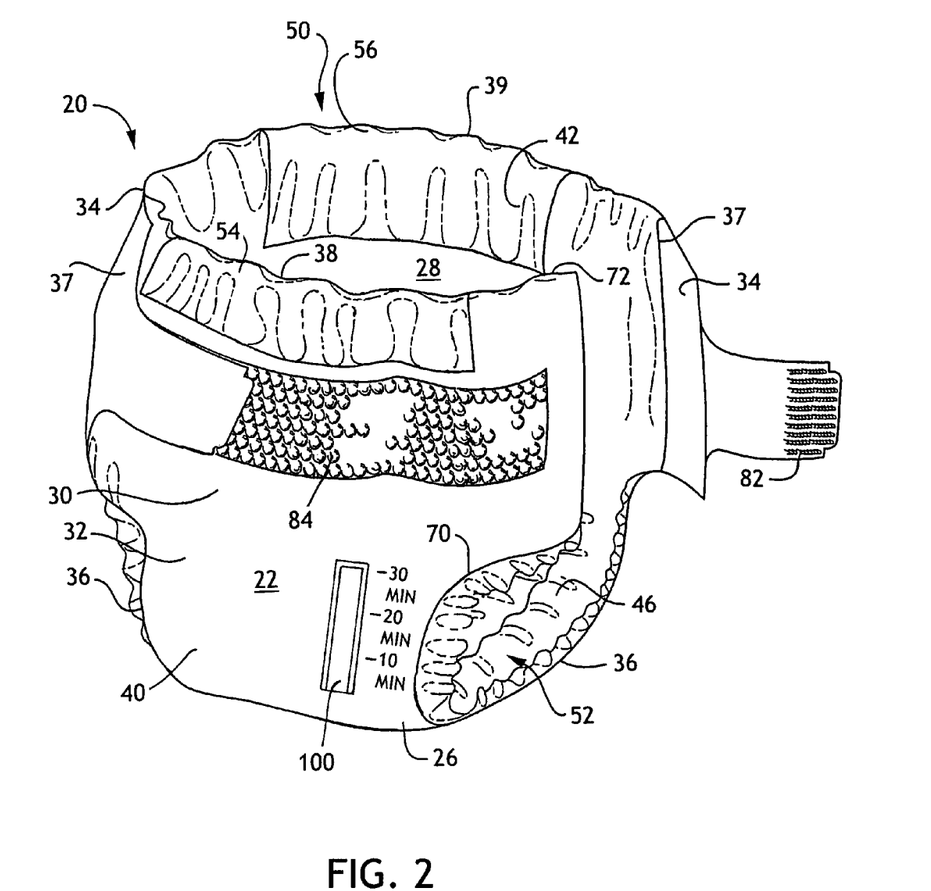
FIG. 2 is a front perspective view of the absorbent article illustrated in FIG. 1.

Referring to FIGS. 1 and 2, for exemplary purposes, an absorbent article 20 that may be made in accordance with the present invention is shown. The absorbent article 20 may or may not be disposable. It is understood that the present invention is suitable for use with various other absorbent articles intended for personal wear including, but not limited to, diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
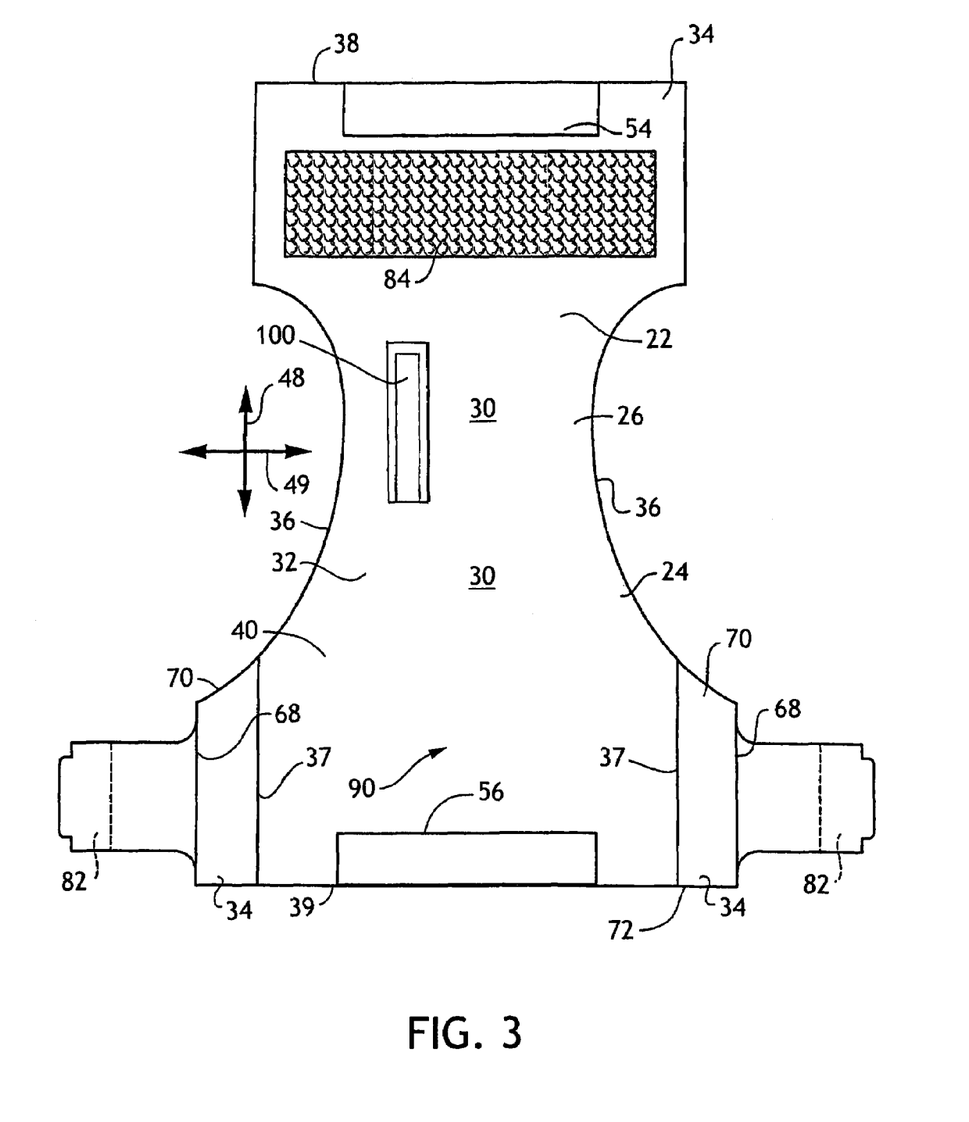
FIG. 3 is a plan view of the absorbent article shown in FIG. 1 with the article in an unfastened, unfolded and laid flat condition showing the surface of the article that faces away from the wearer.
Figure 4:
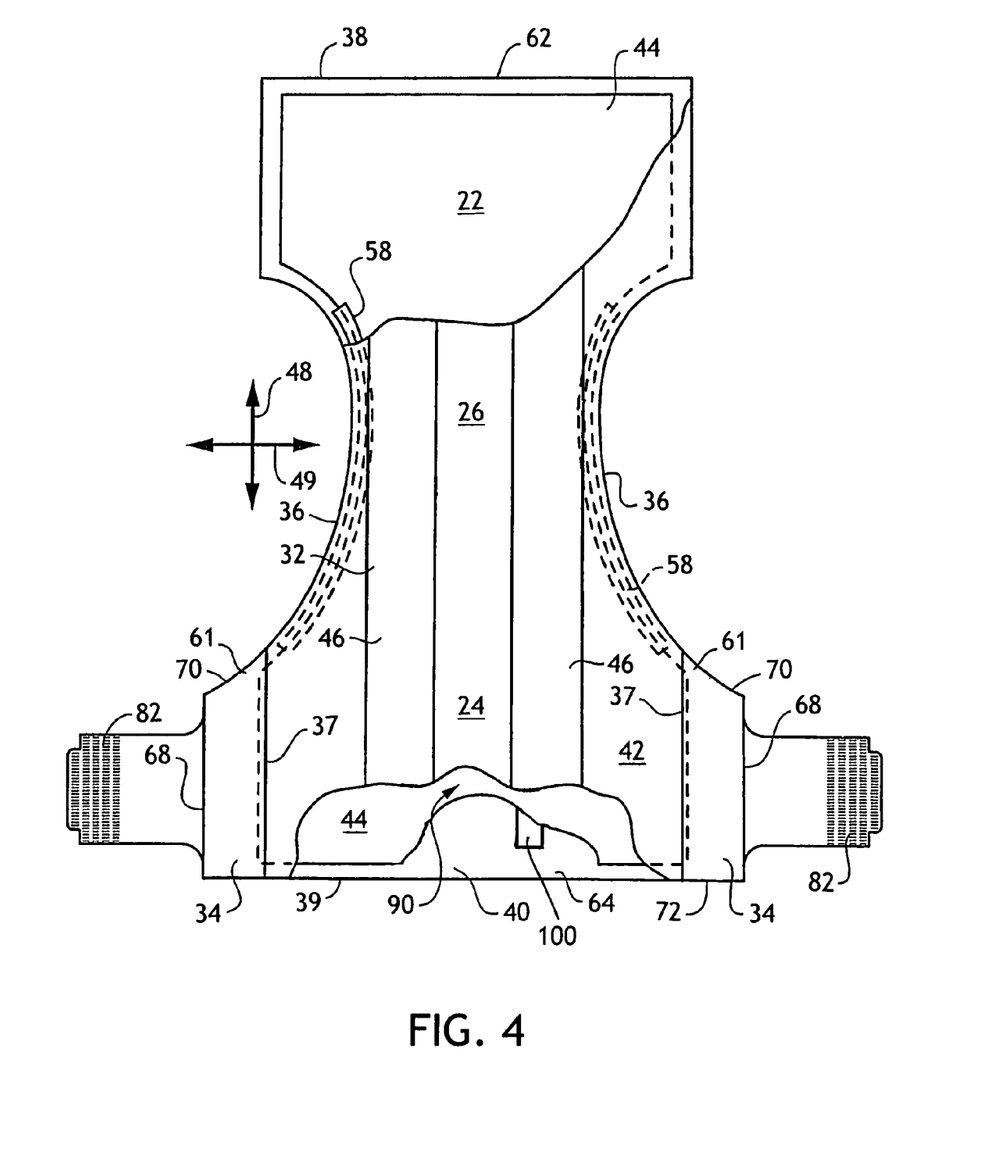
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20, such as the absorbent structure 44 or the bodyside liner 42, by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material, or the like. One skilled in the art will recognize that the shape, density, and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394 and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44. The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

The present disclosure is directed to incorporating a body fluid indicating system into a disposable absorbent article 20. In this regard, as shown in FIGS. 1-7, the absorbent article 20 includes a wicking layer 100 positioned adjacent the outer cover 40. The wicking layer 100 includes a receptive portion 102 and a diagnostic portion 104. At least a portion of the receptive portion 102 of the wicking layer 100 is in liquid communication with the absorbent structure 44. The receptive portion 102 of the wicking layer 100 may be in direct contact with the absorbent structure 44. Alternatively, intermediate materials may connect the receptive portion 102 of the wicking layer 100 and the absorbent structure 44. The absorbent article 20 also includes a liquid barrier 106 positioned between the absorbent structure 44 and a diagnostic portion 104 of the wicking layer 100. The diagnostic portion 104 of the wicking layer 100 is in liquid communication with the receptive portion 102 of the wicking layer 100.

When the absorbent article 20 is insulted with a liquid, such as urine, menses, blood, or the like, the absorbent structure 44 captures and retains the liquid. Conventional absorbent articles 20 are so effective at retaining liquid that caregivers may not know when an absorbent article 20 has been insulted. With traditional products the caregiver does not have any way of determining how much time has elapsed since the absorbent article 20 has been insulted, or how much of the absorbent structure's 44 capacity has been utilized without internal inspection. The wicking layer 100 of the body fluid indication system is in liquid communication with the absorbent structure 44, which addresses these issues. Specifically, an indicator material 108 is located on or near the wicking layer 100. Further, the indicator material 108 comprises a plurality of active constituents, such that the active constituents move along the wicking layer 100 at different speeds as a liquid moves through the wicking layer 100. The indicator material 108 may be located on the diagnostic portion of the wicking layer, or alternatively, the indicator material 108 may be located on the receptive portion 102 of the wicking layer 100. An active constituent as used herein is defined as a portion of the indicator material 108 that is detectable by the caregiver, either alone, or in combination with another portion of the absorbent article 20. For example, an active constituent may be detected visibly (e.g. colored), alternatively, an active constituent may be detected tactilely or audible, when it comes in contact with a second material in the absorbent article.

The indicator material 108 may be a solid or liquid. For example, the indicator material 108 may be an ink where the plurality of active constituents include a first active constituent of a first color and a second active constituent of a second color. The first color and the second color may be different from one another. For example, the first color may be blue and the second color may be yellow. In this example, before liquid moves through the wicking layer 100, the indicator material 108 may appear as a single green mark. As liquid begins to move through the wicking layer 100, the yellow constituent may move more quickly than the blue constituent. By selecting the size of the molecules and the chemical components that make up the molecules of the colored constituent, it is believed that the speed at which the active constituents move may be adjusted. For example, the yellow constituent may move at a relatively high speed, such that the wicking layer 100 quickly becomes yellow along the entire length upon a first insult. The blue constituent may move more slowly such that a single insult will only move the blue constituent a fraction, for example ¼, of the way along the wicking layer 100. In this way, a single indicator material 108 may have dual function, indicating whether or not the article has been insulted, as well as indicating the degree to which the absorbent structure 44 has been utilized.

The indicator material 108 may include active constituents that do not move along the wicking layer 100 when the liquid moves through the wicking layer 100. In this way, the "stationary" active constituent is a reference mark to which the constituents that move may be compared. This may simplify manufacture of the absorbent article 20, in that the indicator material 108 need not be registered to additional marks on the article 20.

As described above, the indicator material 108 may include visible active constituents. Alternatively, the indicator material 109 may comprise active constituents that are invisible. These invisible active constituents may be utilized to create visible changes at locations away from the initial position of the indicator material 108. For example, the absorbent article 20 may include a signal material 110 where contact of the signal material 110 with the invisible active constituent produces a visible change. For example, contact of the signal material 110 with the active constituent may cause the appearance of a color. Alternatively, contact of the signal material 110 with the active constituent may cause a disappearance of a visible signal material, causing the signal material to become clear. Further, the visible change may be a change of color. Chemistries that may be utilized to create this effect include acid/base indicators. For example the invisible active constituent may be either an acid or base, and the signal material may be an acid/base indicator that either becomes visible or clear or changes color depending upon the ph.

In addition to signals that can be detected visually by the caregiver, movement of the active constituents may also be detected by the caregiver either audibly, tactilely, or by using the sense of smell. For example, contact of the active constituent with the signal material 110 may cause a swelling or collapse of the signal material 110, thereby cause a dimensional change in the signal material 110 that may be detectable by the caregiver. Alternatively, contact of the active constituent with the signal material 110 may case a reaction that either creates a sound or produces an aroma which may be detected by the caregiver.

Figure 5:
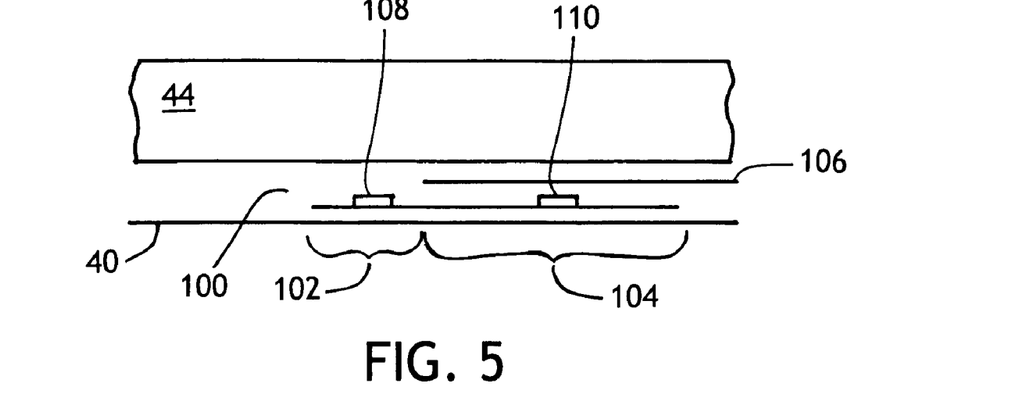
FIG. 5 is a cross sectional view of an embodiment showing an outer cover, absorbent structure, and wicking layer.
Figure 6:
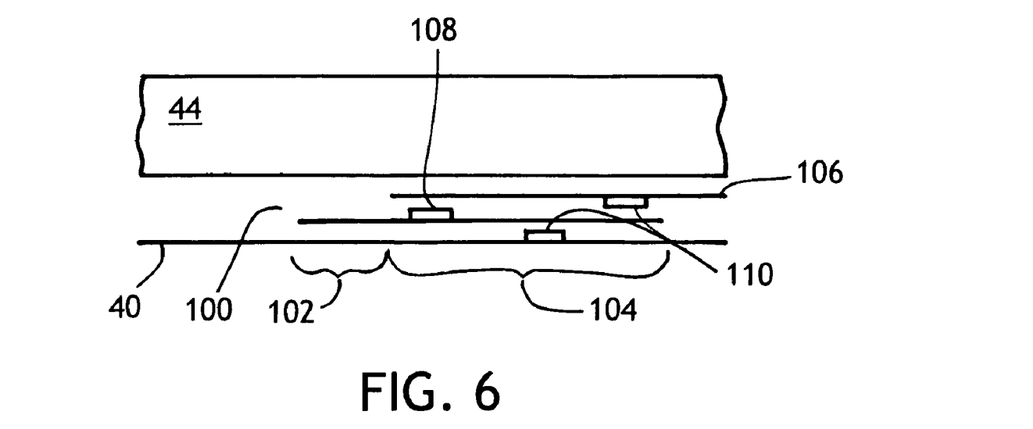
FIG. 6 is a cross sectional view of a second embodiment showing an outer cover, absorbent structure, and wicking layer.
Figure 7:
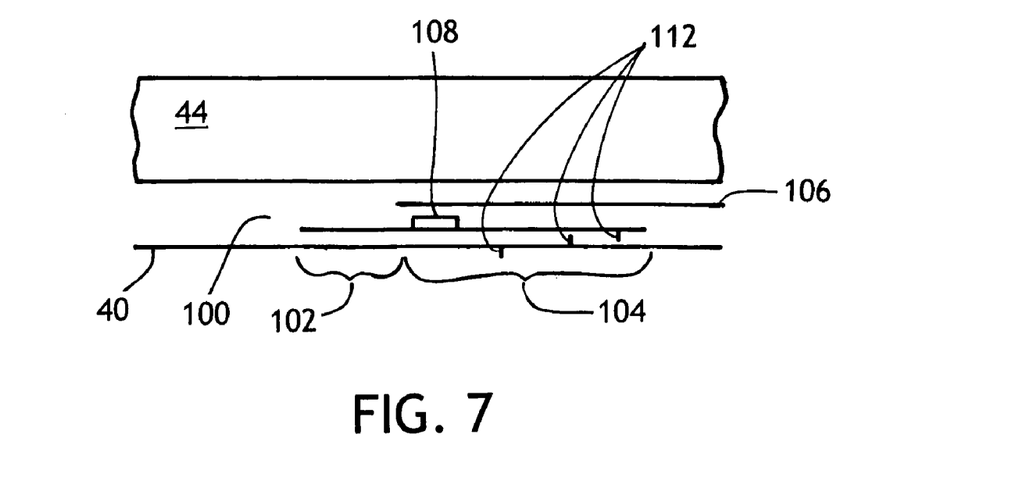
FIG. 7 is a cross sectional view of a third embodiment showing an outer cover, absorbent structure, and wicking layer.

As illustrated in FIGS. 5 and 6, the signal material 110 may be located in various positions in the absorbent article 20. For example, as illustrated in FIG. 5, the signal material 110 may be located on the wicking layer. As illustrated in FIG. 6, the signal material 110 maybe located on the outer cover 40 or the liquid barrier 106. FIG. 6 illustrates a signal material 110 located on the outer cover 40 and the liquid barrier 106. The signal material 110 located on the liquid barrier 106 may be the same as the signal material 110 located on the outer cover 40. Alternatively, the signal material 110 located on the liquid barrier 106 maybe be different than the signal material 110 located on the outer cover 40.

The outer cover 40 adjacent the wicking layer 100 may be translucent to facilitate detection of the wicking layer 100 and active constituents. Alternatively, the outer cover 40 adjacent the wicking layer 100 may be transparent.

The wicking layer 100 may be any suitable material, such as a tissue layer, nonwoven layer, cellulosic materials, treated nonwovens, synthetic fibers, natural fibers, open-celled foam, or the like. Suitable material and construction of the wicking layer 100 may be chosen such that a liquid will move slowly through the wicking layer. This speed at which a liquid moves through the wicking layer 100 may be measured using the vertical wicking test as described below. The wicking layer 100 may have a vertical wicking speed of less than approximately 1.0 cm/min, alternatively less than approximately 0.5 cm/min, or alternatively less than approximately 0.1 cm/min. The low wicking speed of the wicking layer 100 allows for relatively short wicking layers 100 to be utilized to indicate relatively long durations from the time of insult.

The absorbent article 20 may include additional timing indicia 112 positioned on the outer cover 40, wicking layer 100, or barrier layer 106. The timing indicia 112 are located a given time from the indicator material 108 based on the vertical wicking speed. For example, if the vertical wicking speed is 1.0 cm/min, the timing indicia 112 may be located 5 minutes, or 5 cm from the indicator material 108. Alternatively, if the vertical wicking speed is 0.5 cm/min, the timing indicia 112 may be located 20 minutes, or 10 cm from the indicator material 108. In this way the indicator material 108, wicking layer 100, and timing indicia 112 function as a timer to indicate to the caregiver how long that user has been in an insulted article 20. The timing indicia 112 may be positioned any duration of time from the indicator material 108, for example about 5, 10, 15, 20, 30, or 60 minutes from the indicator material 108, based on the vertical wicking speed. The timing indicia 112 may be positioned on the outer cover 40, on the wicking layer 100, or between the wicking layer 100 and the outer cover 40. When the timing indicia 112 are positioned between the wicking layer 100 and the outer cover 40, the timing indicia 112 may include opaque pieces of material which become visible when outlined by the indicator material 108 as it moves through the wicking layer 100. The timing indicia 112 may have any shape, for example, lines, geometric shapes, animal shapes, or the like.

Figure 8:
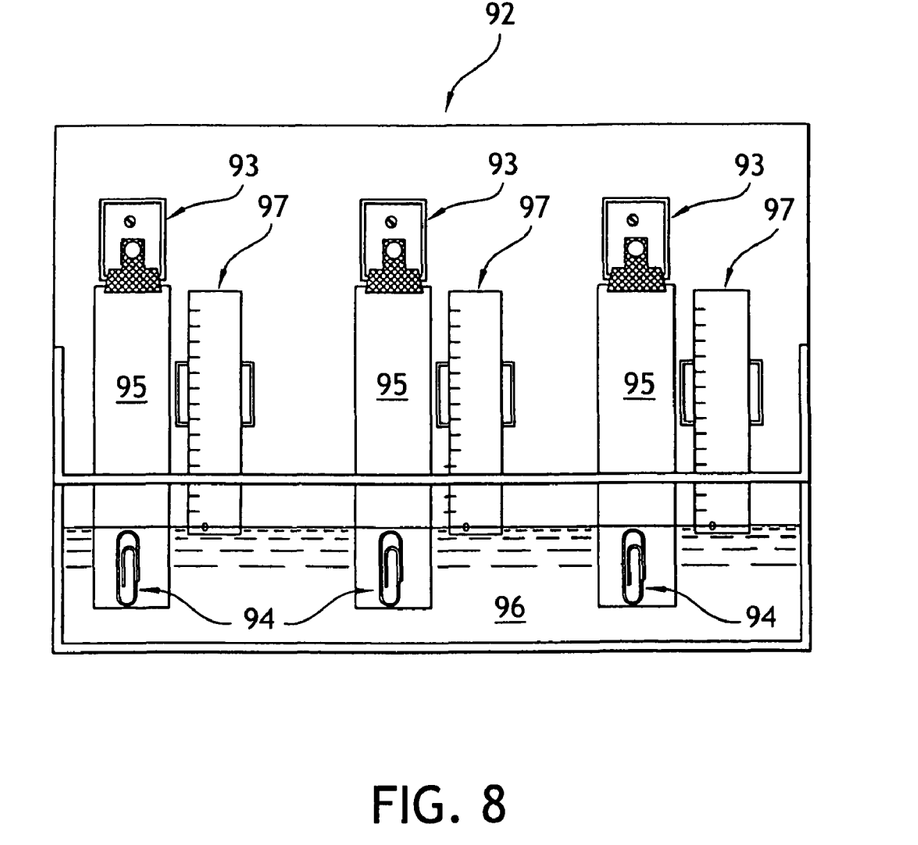
FIG. 8 is a schematic view of the testing apparatus for use with the vertical wicking test.

Vertical Wicking Test: The vertical wicking test measures the height of water that can be vertically wicked by the sample in a given period of time. A reservoir containing purified distilled/deionized water is provided. One end of a 25 mm×203 mm (1 inch×8 inch) specimen is clamped to a support block 93 and the other end is placed in the fluid such that it extends 2.5 cm therein. An apparatus 92 can be used similar to that depicted in FIG. 8. A paper clip 94 or other weight may be used to weight the lower end of the specimen 95 in order to prevent the specimen from curling and allow the lower end of the specimen to readily submerge into the water 96 in the reservoir. Support blocks 93 maintain the specimen at a fixed height. The time it takes for the liquid to migrate from 1 centimeter above the liquid surface to 6 centimeters above the liquid surface is measured. Taking 5 cm divided by this time results in the vertical wicking speed and is reported in cm/min. A ruler 97 or other device can be used to determine the degree of liquid migration up the specimen. Tests are conducted in a laboratory atmosphere of 23+/−1 degrees C. and 50+/−5% RH. The vertical wicking speed for a sample is given as the average of at least three specimens. These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An absorbent article for absorbing a liquid comprising:
    a chassis comprising an outer cover having an interior surface and an exterior surface and an absorbent structure positioned adjacent the interior surface of the outer cover, the chassis including a crotch region positioned in between a front region and a back region, the front region and the back region defining a waist region therebetween;
    a wicking layer positioned adjacent the outer cover, wherein at least a receptive portion of the wicking layer is in liquid communication with the absorbent structure;
    a liquid barrier positioned between the absorbent structure and a diagnostic portion of the wicking layer, the diagnostic portion of the wicking layer being in liquid communication with the receptive portion of the wicking layer; and
    an indicator material located on the wicking layer, the indicator material comprising a plurality of active constituents, wherein the active constituents move along the wicking layer at different speeds as the liquid moves through the wicking layer, and wherein the wicking layer has a vertical wicking speed of less than 0.5 cm/min.

2. The absorbent article of claim 1 further comprising a timing indicia positioned from about 5 minutes to about 30 minutes from the indicator material based on the vertical wicking speed.

3. The absorbent article of claim 2 wherein the timing indicia is positioned on the outer cover.

4. The absorbent article of claim 2 wherein the timing indicia is positioned on the wicking layer.

5. The absorbent article of claim 2 wherein the timing indicia is positioned between the wicking layer and the outer cover.

6. The absorbent article of claim 1 wherein the indicator material is located on the diagnostic portion of the wicking layer.

7. The absorbent article of claim 1 wherein the plurality of constituents include a first active constituent of a first color and a second active constituent of a second color, the first color and the second color being different from one another.

8. The absorbent article of claim 1 wherein at least one of the plurality of active constituents does not move along the wicking layer when the liquid moves through the wicking layer.

9. The absorbent article of claim 1 wherein the plurality of active constituents comprises visible constituents.

10. The absorbent article of claim 1 wherein the plurality of active constituents comprises invisible constituents.

11. The absorbent article of claim 10 further comprising a signal material, wherein contact of the signal material with the invisible active constituent produces a visible change.

12. The absorbent article of claim 11 wherein the visible change is an appearance of a color, a disappearance of a color, or a change of color.

13. The absorbent article of claim 11 wherein the signal material is located on the outer cover, the liquid barrier, or the wicking layer.

14. The absorbent article of claim 1 wherein the outer cover adjacent the wicking layer is translucent or transparent.

* * * * *